(12) United States Patent  
Alon et al.

(10) Patent No.: US 6,625,495 B1
(45) Date of Patent: Sep. 23, 2003

(54) BODY-CAVITY PROBE WITH BODY CONFORMABLE MEMBER

(75) Inventors: Gad Alon, Rockville, MD (US); Avraham Cohen, Charev Laet (IL)

(73) Assignee: Medisox Israel Ltd., Yokneam-Elit (IL)

( * ) Notice: Subject to any disclaimer, the term of this patent is extended or adjusted under 35 U.S.C. 154(b) by 76 days.

(21) Appl. No.: 09/631,123

(22) Filed: Aug. 2, 2000

(51) Int. Cl.$^7$ ................................................ A61N 1/05
(52) U.S. Cl. .................. 607/116; 607/138; 607/149; 600/373; 600/587; 600/591; 600/325; 600/561
(58) Field of Search .................. 607/116, 138, 607/149, 2, 39, 40, 41; 600/301, 372, 373, 376, 587, 593, 323, 325, 561, 591

(56) References Cited

U.S. PATENT DOCUMENTS

| | | | |
|---|---|---|---|
| 5,184,619 A | * 2/1993 | Austin | 600/376 |
| 5,385,577 A | 1/1995 | Maurer et al. | |
| 5,417,207 A | * 5/1995 | Young et al. | 600/323 |
| 5,483,832 A | * 1/1996 | Pauser et al. | 73/379.08 |
| 5,662,699 A | * 9/1997 | Hamedi et al. | 607/138 |
| 5,702,428 A | * 12/1997 | Tippey et al. | 607/41 |
| 5,733,230 A | * 3/1998 | Sawchuck et al. | 482/111 |

FOREIGN PATENT DOCUMENTS

| | | |
|---|---|---|
| FR | 2790379 | 3/1995 |
| GB | 2301287 | 12/1996 |

* cited by examiner

Primary Examiner—Kennedy Schaetzle
(74) Attorney, Agent, or Firm—G.E. Ehrlich (1995) Ltd

(57) ABSTRACT

A probe insertable into a body cavity for applying an electrical stimulation to tissue therein includes a flexible hollow member of biocompatible material to enable the member to be inserted into the body cavity and to substantially conform to its inner surface, and thereby, to contact the tissue therein to be stimulated. A portion of the outer surface of the hollow member is electrically conductive to enable an electrical voltage to be applied thereto for electrically stimulating the tissue within the body cavity contacted by the electrically conductive surface. The probe may also include a transparent section and an optical sensor, such as an oximeter, for optically examining tissues within the body cavity.

11 Claims, 2 Drawing Sheets

BODY-CAVITY PROBE WITH BODY CONFORMABLE MEMBER

FIELD OF THE INVENTION

The present invention relates to probes insertable into a body cavity for various purposes, as will be described more particularly below, and also to a method of utilizing such a probe for the various purposes described below.

The invention may be used to apply any combination of electrical stimulation, pressure biofeedback, and microcirculation biofeedback for therapeutic purposes as well as to make measurements of pelvic floor muscular and vascular impairments. The therapeutic purposes include treating for impairments or dysfunsctions of the neuro-muscular, neurovascular, peripheral vascular systems associated with bladder and fecal incontinence, disuse atrophy and weakness of the pelvic floor musculature, pelvic pain, erectile dysfunction, and orgasm.

BACKGROUND OF THE INVENTION

It is well know to apply electrotherapy over the pelvic floor surface, or within the vagina or rectum, in order to improve, ameliorate or prevent impairments of the pelvic floor such as muscle disuse atrophy, urine or bowel incontinence, or pelvic pain, hereinafter collectively referred to as pelvic floor dysfunction; see for example: FALL, Magnus, Advantages and Pitfalls of Functional Electrical Stimulation, *Acta Obstet Gynecol Scand* 1998; Supplement 168: 77:16–21; and BO, Karl, Effect of Electrical Stimulation on Stress and Urge Urinary Incontinence, *Acta Obstet Gynecol Scand* 1998; Supplement 168: 77:3–11, both hereby incorporated herein by reference.

Currently, there are various probe designs that measure vaginal or rectal electromyographic (EMG) activity of the pelvic floor musculature. There are also several electrically conductive probes that deliver pulses of electrical energy aimed at depolarization and excitation of the nerves and muscle fibers of the pelvic floor and associated structures. The purpose of such stimulation is to help in the treatment of incontinence or pelvic pain. It is also known to provide electrically conductive electrodes in a probe for the dual purpose of either stimulation of, or recording, muscular activity (EMG) in the pelvic floor musculature. Generally, the probes to measure pressure are inflatable in order to establish intimate contact with the vaginal or rectal walls; and the probes for electrical stimulation or EMG recordings are constructed as rigid bodies.

There are several drawbacks in the existing probes. Having a rigid body presents a major disadvantage because the contracting muscles cannot shorten while contracting, and as a result they may not effectively stop the leakage. Inflating a pressure probe presents a similar disadvantage. Furthermore the rigid body of the probe does not permit an even contact with the irregular and highly variable surfaces of the vagina or rectum. These shortcomings may result in a very uncomfortable stimulation due to high current density.

Another deficiency in existing probes is the inability to measure the contractile force simultaneously with the application of electrical stimulation. Consequently neither the patient nor the clinician can determine how much if any contractile force is induced by the stimulation, and thus how effective is the stimulation. Measuring EMG during contraction may not correlate with the amount of contractile force, thus making it very difficult to quantify the strength of the pelvic floor musculature. Moreover, the known probes and stimulation EMG systems do no permit concurrent stimulation and EMG recording from the pelvic musculature. Finally, available pressure probes are not designed to conduct electricity and thus cannot be used simultaneously with electrical stimulation, a combination that may enhance significantly the recovery of muscle strength.

OBJECTS AND BRIEF SUMMARY OF THE INVENTION

An object of the present invention is to provide a body-cavity probe having advantages in one or more of the above respects. Another object of the invention is to provide a method for utilizing such a probe in order to treat for any one of a plurality of pelvic floor dysfunctions.

According to one aspect of the present invention, there is provided a probe insertable into a body cavity for applying an electrical stimulation to tissue therein, comprising: a hollow member of flexible biocompatible material to enable the member to be inserted into the body cavity and to substantially conform to its inner surface, and thereby, to contact the tissue therein to be stimulated; at least a portion of the outer surface of the hollow member being electrically conductive to enable an electrical voltage to be applied thereto for electrically stimulating the tissue within the body cavity contacted by the electrically conductive surface.

More particularly, in the described preferred embodiments the hollow member includes at least two sections of electrically-conductive biocompatible material separated from each other by sections of electrically-insulating biocompatible material. Preferably, the hollow member is made of sections of electrically-conductive and electrically-insulating silicon resin.

According to further features in the described preferred embodiment, the hollow member is of tubular configuration, closed at one end and open at the opposite end to face the outer end of the body cavity to permit a fluid within the hollow member to be expelled, and thereby to permit the hollow member to substantially conform to the inner surface of the body cavity.

In the described preferred embodiments, the hollow member further includes a central spine of relatively stiff material extending through the interior of the hollow member. One end of the central spine includes a dome-shaped tip engaging the inner surface of the closed end of the hollow member, and the opposite end of the central spine includes a base secured to the open end of the hollow member. The base of the central spine includes an enlarged plate to be located externally of the body cavity and thereby to limit the penetration of the hollow member into the body cavity. The dome shaped tip of the central spine is electrically-conductive, and the closed end of the hollow member is also electrically-conductive. The central spine may be used for supporting the electrical conductors to the respective electrically-conductive sections of the hollow member.

According to still further features in the described preferred embodiments, the base includes a tube having one end communicating with the interior of the hollow member for the passage of fluids thereinto or therefrom, and an opposite end leading out of the hollow member and of the body cavity when the hollow member is inserted therein. The opposite end of the tube is connected to a fluid pressure measuring device for measuring the fluid pressure within the hollow member, and thereby the pressure applied to the hollow member by the tissue within the body cavity contacted by the hollow member.

The probe may also be used for inserting an optical sensor into the body cavity.

According to another aspect of the present invention, therefore, there is provided a probe insertable into a body cavity for sensing a condition therein, comprising: a hollow member of flexible biocompatible material such that the member, upon insertion into the body cavity, substantially conforms to the inner surface of the body cavity; at least a portion of the hollow member being optically transparent; and an optical sensor within the hollow member and aligned with the transparent section to optically sense a condition within the body cavity.

According to yet another aspect of the invention, there is provided a method of applying electrical stimulation to tissue within a body cavity, comprising: inserting into the body cavity a hollow member of flexible biocompatible material such that the hollow member substantially conforms to the inner surface of the body cavity and contacts the tissue therein to be stimulated, at least a portion of the outer surface of the hollow member being electrically conductive; and applying an electrical voltage to the electrically-conductive surface of the body member for electrically stimulating the tissue within the body cavity contacted by the electrically conductive surface.

According to a still further aspect of the invention, there is provided a method of sensing a condition of tissue within a body cavity, comprising: inserting into the body cavity a hollow member of flexible biocompatible material substantially conforming to the inner surface of the body cavity and thereby contacting the tissue therein whose condition is to be sensed, at least a portion of the hollow member being optically transparent, there being an optical sensor within the hollow member in alignment with the optically-transparent section; and utilizing the optical sensor for optically sensing a condition within the body cavity.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
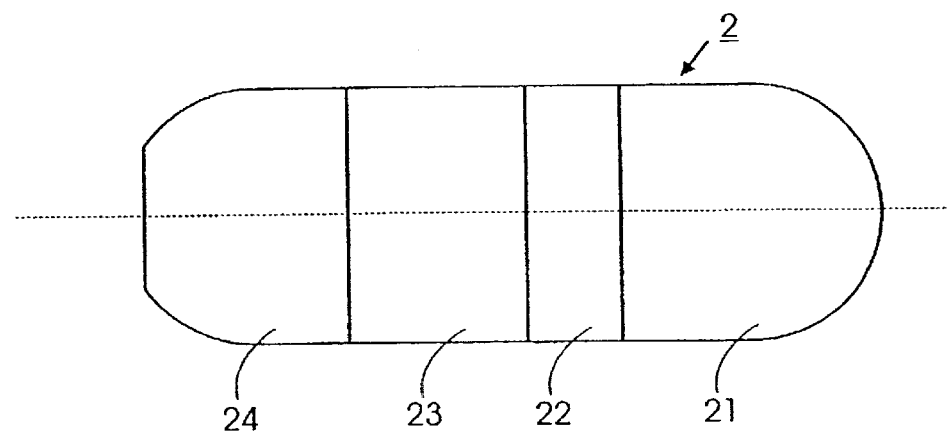
FIG. 1 is a side view illustrating one form of probe constructed in accordance with the present invention.
Figure 2:
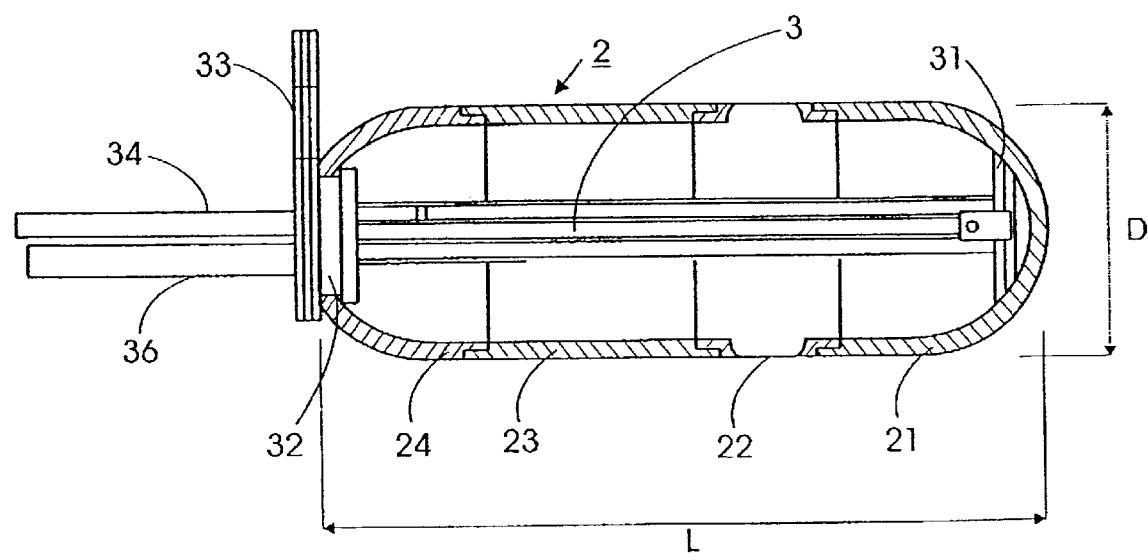
FIG. 2 is a view, partly in section, more particularly illustrating the construction of a probe in accordance with the present invention.
Figure 3:
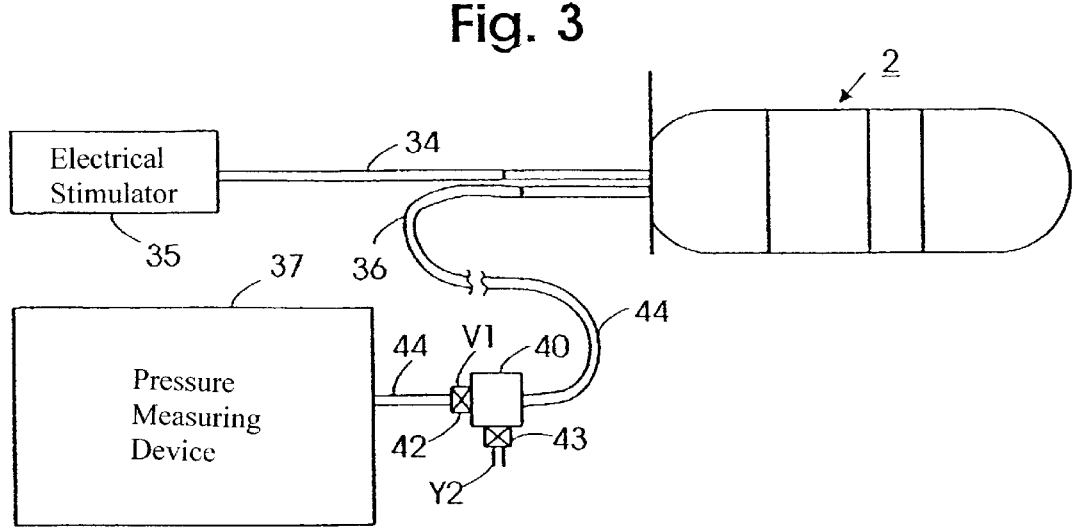
FIG. 3 illustrates a system, including the probe of FIG. 2, for electrically stimulating the muscles of the pelvic floor or for measuring the contractile force applied by the muscular tissue thereat.

The probe illustrated in FIGS. 1–3 of the drawings and therein generally designated 2 is designed for insertion into a body cavity, such as the vagina of a female or the anus of a female or male, for applying an electrical stimulation to the muscles of the pelvic floor, and/or for measuring a condition therein, e.g., for the treatment of any one of a plurality of pelvic floor dysfunctions, such as urine and fecal incontinence, pelvic pain, erectile dysfunction, and orgasm. It includes a flexible hollow member of a flexible biocompatible material which, when inserted into the respective body cavity (e.g., vagina or anus), substantially conforms to the inner surface of the body cavity so as to be in contact with the tissue therein to be stimulated or to be examined.

A particularly suitable material is a biocompatible silicon resin, such as used in baby nipples, pacifiers, and the like, providing a structure which is substantially self-supporting but sufficiently flexible and supple so as to respond readily to changes in the surface of the body cavity into which the hollow member is inserted. Although the flexible hollow probe 2 is substantially self-supporting, it is provided with a central spine, generally designated 3, serving to further support the hollow probe, as well as to provide other functions during the use of this probe for stimulation and/or measurement purposes, as will be described more particularly below.

As seen particularly in FIG. 2, the flexible hollow probe 2 is made of four sections, all joined together, to produce a tubular configuration closed at one end and open at the other end. Thus, hollow probe 2 includes a dome-shaped section 21 at the closed end joined by two annular sections 22, 23, the latter being joined to another section 24 constituting the open end of the hollow probe. All four sections 21–24 of the hollow probe 2 are preferably made of a biocompatible silicon resin and are joined in any suitable manner, as by a suitable adhesive. Sections 21 and 23, however, of the hollow probe are made electrically-conductive, as by the provision of electrically-conductive particles, preferably carbon, in the resin. Such electrically-conductive particles are not included in the resin to produce section 22 and 24, so that those sections are electrically-insulating, and thereby insulate the two electrically-conductive sections 21 and 23 from each other.

For purposes of example, the flexible hollow probe 2 may be made of medical grade silicon of a thickness of 0.1 to 2 mm, of a diameter (D) that may range from 10 mm to 40 mm, and a length (L) that may range from 30 to 150 mm, depending on the specific application of the probe.

The central spine 3 is made of a stiff material, such as plastic, but is not limited to this material. It may have a diameter ranging from 2 mm to 10 mm, and extends for the complete length (L) of the hollow probe 2. Its inner end or tip 31 is dome-shaped, conforming to the dome-shaped section 21 of the hollow probe, and is made of electrically-conductive material, such as copper or stainless steel, to provide good electrical contact with the electrically-conductive section 21 of the hollow probe.

The opposite end of the stem 3 is formed as a base 32 of stiff rigid material and is secured to the open end of the flexible hollow probe 2. The base 32 is further secured to an enlarged plate 33 externally of the hollow probe 2 so as to be located externally of the body cavity in which the hollow probe is inserted, to limit the penetration of the hollow probe 2 into the body cavity.

The central spine 3 further includes a cable 34 having one electrical conductor connected to the electrically-conductive dome 31 in contact with the electrically-conductive end 21 of the flexible hollow probe 2, and another electrical conductor connected to the electrically-conductive section 23 of the hollow probe. As shown in FIG. 3, cable 34 is connected to an electrical stimulator 35 which applies the electrical voltages to the electrically-conductive sections 21 and 23 of the hollow probe 2 for stimulating the muscle tissue in contact with those sections of the hollow probe.

The flexible hollow probe 2 further includes a fluid tube 36 having one end communicating with the interior of the hollow probe, and the opposite end communicating with a pressure-measuring device, shown at 37 in FIG. 3.

As further shown in FIG. 3, tube 36 is connected to the pressure-measuring device 37 via a fitting 40, which may be of a Y-type or a T-type, including an inlet 41 and two outlets 42, 43. Outlet 42 is connected via a valve $V_1$ to the inlet tube 44 to the pressure measuring device 37. Outlet 43 is connected via a second valve $V_2$ to the atmosphere. Valve $V_1$ is a simple shut-off valve which may be opened or closed; whereas valve $V_2$ is one-way valve which, when opened, allows fluid to pass only outwardly into the atmosphere as shown by the arrow, but may also be closed.

The probe illustrated in FIGS. 1–3 may be used in the following manner.

With valve $V_1$ closed, and valve $V_2$ opened, the flexible hollow probe 2 is inserted into the body cavity, e.g., vagina or anus, to be electrically stimulated or examined. Since valve $V_2$ is opened, it permits the exit of air caused by the contraction of the probe when conforming its outer surface to the inner surface of the body cavity.

After the probe has thus been inserted, valve $V_2$ is closed, and valve $V_1$ is opened, thereby establishing two-way communication between the interior of the probe and the fluid pressure measuring device 37. Accordingly, contractions or relaxations of the muscle tissue contacted by the outer surface of the probe will cause changes in pressure within the probe, which changes in pressure will be measured by the pressure measuring device 37.

Before, during, or after, the measurement of pressure changes within the probe 2, the electrical stimulator 35 may be operated to apply electrical voltages to the electrically-conductive sections 21 and 23 of the probe, to thereby stimulate the tissue in contact with those sections of the probe.

It will be appreciated that once valve $V_2$ is closed and valve $V_1$ is opened, the measuring device 37 is connected to the interior of the probe, and the entire system is otherwise sealed to prevent penetration of air, thus keeping the probe in its original contracted condition. This contraction of the probe causes its shape to conform intimately to the walls of the body cavity (vagina or rectum), thus creating optimum contact for the stimulating electrically-conductive sections, more responsive pressure measurements, and better anchoring of the probe inside the body cavity.

The stimulator 35 may be one of the commercially available neuromuscular electrical stimulators (NMES). It can be used to stimulate the pelvic floor musculature and, simultaneously or independently, measure the contractile force of the pelvic floor musculature. The measured force may be displayed on the display unit and used to provide the subject with immediate or delayed information, analog or digital, regarding the results. It likewise provides the clinician with objective measurements of pelvic floor contractile force.

The measuring unit 37 may also be a commercially available device. Such devices commonly include pressure sensors, standard analog-to-digital circuitry that converts the pressure-generated voltage changes into digital output, and electronic displays. Examples of such devices are those supplied by Enteran Devices, Inc., of Fairfield, N.J.

To obtain measurements, or to stimulate the muscles of the pelvic floor, vagina, and rectum, the subject inserts the probe into the vagina or rectum. The measuring unit is calibrated to zero (0) pressure, and the measurements of pressure changes and time of contraction are recorded and stored.

To activate the stimulator, the subject connects the two leads of the stimulator output to the probe, and increases stimulator intensity using the appropriate stimulus parameters to induce excitation of sensory and motor nerves (or direct excitation of muscle fibers) that results in either twitch or tetanic muscle contraction. The subject can then use the probe to only stimulate or to only measure volitional or spontaneous contraction force of the pelvic floor, or can combine the stimulation with the force measurements.

Figure 4:
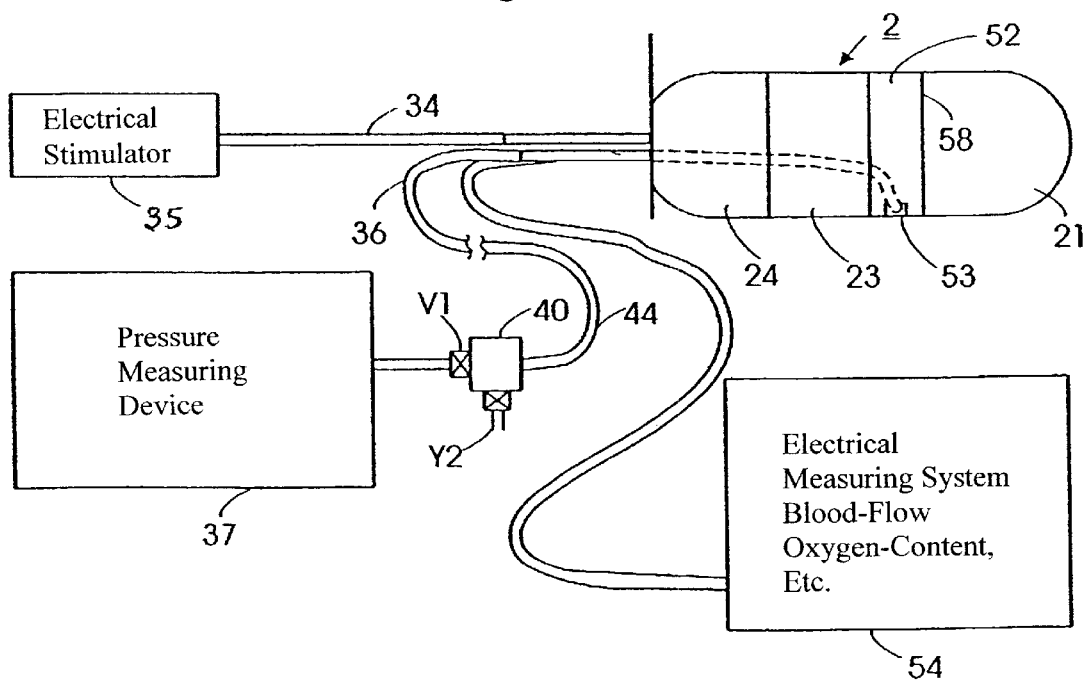
FIG. 4 illustrates a system, similar to that of FIG. 3, but also including an optical sensor for sensing a condition within the body cavity, such as the flow or oxygen-content of blood flowing through tissue therein.

FIG. 4 illustrates a variation in the construction of the probe of FIGS. 1–3. In this variation, one of the insulating sections of the probe, such as insulating section 22, may be made light-transparent and used for mounting an optical sensor within the probe. FIG. 4 illustrates this transparent section identified by the reference numeral 52, and the optical sensor 53 mounted thereon and in optical alignment therewith. The optical sensor may be, for example, an oximeter to optically sense the flow, or oxygen-content, of the blood flowing through tissue in the body cavity contacted by section 52 of the probe. Accordingly, oximeter 53 is connected to electrical measuring system 54 for measuring the optical condition sensed by the oximeter, and for translating such measurements into blood flow, oxygen-content, or any other condition for which oximeters are commonly used.

In all other respects, the system illustrated in FIG. 4 is constructed and operates in the manner described above, and therefore the same reference numerals have been used to simplify the description.

While the invention has been described with respect to two preferred embodiments, it will be appreciated that these are set forth merely for purposes of example, and that many variations, modifications and other applications of the invention may be made. For example, the invention may be used only for one or two of the above-described functions, i.e., for applying electrical stimulation to tissues within a body cavity, and/or for using pressure-sensitive means for measuring changes in the body cavity and/or for using optical-sensing means for measuring changes in the body cavity. In addition, while the probe is shown as being filled with air, it could be filled with another fluid, such as a saline liquid, to make the probe more sensitive to pressure variations, but in such case the inner surfaces of the electrically-conductive sections of the probe would have to be insulated.

Many other variations, modifications and applications of the invention will be apparent.

What is claimed is:

1. A probe insertable into a body cavity for applying electrical stimulation to tissue therein, characterized in comprising:

a hollow member of tubular configuration and of flexible biocompatible material to enable the member to be inserted into the body cavity and to substantially conform to its inner surface, and thereby to contact muscle tissue therein to be stimulated;

said hollow member being closed at one end and open at the opposite end to face the outer end of the body cavity to permit a fluid within the hollow member to be expelled and thereby to permit the conformity of the hollow member to the inner surface of the body cavity;

at least a portion of the outer surface of said hollow member being electrically-conductive to enable an electrical voltage to be applied thereto for electrically stimulating the muscle tissue within the body cavity contacted by the electrically-conductive surface;

said opposite end of the tube including a one-way valve permitting only the exit of fluid from the hollow member to allow the hollow member to conform to the inner surface of the body cavity upon the insertion of the hollow member into the body cavity, said one-way valve being closable to allow measurement of changes in fluid pressure within the hollow member, and thereby changes in pressure resulting from contractions or relaxations of the muscle tissue contacted and electrically stimulated by said probe.

2. A probe according to claim 1, characterized in that said hollow member is made of sections of electrically-conductive and electrically-insulating silicon resin.

3. A probe according to claim 1, characterized in that said hollow member further includes a central spine of relatively stiff material extending through the interior of the hollow member from said closed end to said open end.

4. A probe according to claim 3, characterized in that one end of the central spine includes a dome-shaped tip engaging the inner surface of the closed end of the hollow member, and the opposite end of the central spine includes a base secured to the open end of the hollow member.

5. A probe according to claim 4, characterized in that the said base of the central spine includes an enlarged plate to be located externally of the body cavity and thereby to limit the penetration of the hollow member into the body cavity.

6. A probe according to claim 4, characterized in that said dome-shaped tip of the central spine is electrically-conductive, and said closed end of the hollow member is also electrically-conductive.

7. A probe according to claim 6, characterized in that said hollow member further includes an electrically-conductive section spaced from said electrically-conductive closed end by an electrically-insulating section.

8. A probe according to claim 7, characterized in that said central spine further includes electrical conductors connected to said electrically-conductive section and said electrically-conductive closed end of the hollow member.

9. A probe according to claim 1, characterized in that it further comprises a fluid pressure measuring device communicating with said open end of the hollow member for measuring the changes in pressure resulting from contractions or relaxations of the muscle tissue contacted and electrically stimulated by said probe.

10. A probe according to claim 1, characterized in that said hollow member further includes an optically-transparent section, and an optical sensor within the hollow member and optically aligned with said transparent section to optically sense a condition within the body cavity.

11. A probe according to claim 10, characterized in that said optical sensor is an oximeter to optically sense the flow or oxygen content of blood flowing through tissue in the body cavity.

* * * * *